(12) United States Patent
Liu et al.

(10) Patent No.: US 11,672,496 B2
(45) Date of Patent: Jun. 13, 2023

(54) IMAGING SYSTEMS AND METHODS

(71) Applicant: SHANGHAI UNITED IMAGING HEALTHCARE CO., LTD., Shanghai (CN)

(72) Inventors: Shitao Liu, Shanghai (CN); Jinlong Li, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 141 days.

(21) Appl. No.: 17/114,545

(22) Filed: Dec. 8, 2020

(65) Prior Publication Data

US 2021/0169432 A1  Jun. 10, 2021

(30) Foreign Application Priority Data

Dec. 9, 2019  (CN) .......................... 201911248990.X
Mar. 11, 2020 (CN) ........................... 202020292269.2

(51) Int. Cl.
*G06T 7/73* (2017.01)
*A61B 6/00* (2006.01)
(Continued)

(52) U.S. Cl.
CPC ............ *A61B 6/488* (2013.01); *G06T 7/0014* (2013.01); *G06T 7/73* (2017.01); *G06V 10/22* (2022.01); *G06V 40/10* (2022.01); *A61B 5/0013* (2013.01); *A61B 5/704* (2013.01); *A61B 6/0407* (2013.01); *A61B 6/563* (2013.01); *G06T 2207/10081* (2013.01); *G06T 2207/10088* (2013.01); *G06T 2207/10104* (2013.01); *G06T 2207/30004* (2013.01)

(58) Field of Classification Search
CPC ...... G06V 40/10; G06V 10/751; G06F 3/167; G06T 7/0014; G06T 7/73; G06T 2207/30004; G06T 2207/10081; G06T 2207/10088; G06T 2207/10104; A61B 5/055; A61B 5/4561; A61B 5/704; A61B 5/0013; A61B 5/0037; A61B 6/563; A61B 6/0407; A61B 6/037; A61B 6/032; A61B 6/488

See application file for complete search history.

(56) References Cited

U.S. PATENT DOCUMENTS 9,466,133 B2 * 10/2016 Sowards-Emmerd ........................ A61B 6/037
2002/0118280 A1 * 8/2002 Medlar .................. H04N 7/181
348/E7.086
(Continued)

FOREIGN PATENT DOCUMENTS

CN   101551906 A   10/2009
CN   105227802 A   1/2016
(Continued)

*Primary Examiner* — Shefali D Goradia
(74) *Attorney, Agent, or Firm* — Metis IP LLC

(57) ABSTRACT

The present disclosure is related to imaging systems and methods. The method includes obtaining image data of a subject to be scanned by a medical device. The method includes determining a scan range of the subject based on the image data. The scan range includes at least one scan area of the subject. The method includes determining at least one parameter value of at least one scan parameter based on the at least one scan area of the subject.

20 Claims, 6 Drawing Sheets

(51) Int. Cl.
*G06T 7/00* (2017.01)
*G06V 40/10* (2022.01)
*G06V 10/22* (2022.01)
*A61B 5/00* (2006.01)
*A61B 6/04* (2006.01)

(56) References Cited

U.S. PATENT DOCUMENTS

| | | | | |
|---|---|---|---|---|
| 2009/0076379 | A1* | 3/2009 | Hamill | A61B 6/032 |
| | | | | 600/463 |
| 2009/0285357 | A1* | 11/2009 | Khamene | A61B 6/5217 |
| | | | | 378/207 |
| 2015/0119703 | A1* | 4/2015 | Mitchell | A61B 6/5294 |
| | | | | 600/425 |
| 2016/0183905 | A1 | 6/2016 | Lou et al. | |
| 2017/0112416 | A1 | 4/2017 | Hao et al. | |
| 2017/0173262 | A1* | 6/2017 | Veltz | G16H 20/17 |
| 2018/0250183 | A1* | 9/2018 | Zwierstra | A61B 8/0808 |

FOREIGN PATENT DOCUMENTS

| | | | |
|---|---|---|---|
| CN | 107273885 A | 10/2017 | |
| CN | 107320124 A | 11/2017 | |
| CN | 107334487 A | 11/2017 | |
| CN | 107510468 A | 12/2017 | |
| CN | 109381212 A | 2/2019 | |
| CN | 109549659 A | 4/2019 | |
| CN | 109717886 A | 5/2019 | |
| KR | 101525040 B1 * | 5/2015 | A61B 6/5205 |

* cited by examiner

IMAGING SYSTEMS AND METHODS

CROSS-REFERENCE TO RELATED APPLICATIONS

This application claims priority of Chinese Patent Application No. 201911248990.X, filed on Dec. 9, 2019, and Chinese Patent Application No. 202020292269.2, filed on Mar. 11, 2020, the contents of each of which are hereby incorporated by reference.

TECHNICAL FIELD

This disclosure generally relates to systems and methods for medical imaging, and more particularly, relates to systems and methods for determining posture information and a scan parameter of a subject.

BACKGROUND

Medical systems, such as CT scanners, MRI scanners, PET scanners, are widely used for creating images of interior of a patient's body for medical diagnosis and/or treatment purposes. Generally, a medical system usually needs to know posture information (e.g., whether the patient is lying in a prone or supine posture) of a patient before, during, and/or after the medical system performs a scan on the patient. For example, one or more scan parameters of the patient may be determined and/or adjusted based on the posture information of the patient. As another example, the position information of the patient may be displayed in a medical image generated based on the scan of the patient for subsequent disease diagnosis. In addition, during the scan of the patient, different scan areas of the patient may correspond to different parameter values of scan parameters. Thus, it is desirable to develop methods and systems for determining posture information and scan parameter(s) of a subject in a medical system.

SUMMARY

According to an aspect of the present disclosure, a method may be implemented on a computing device having at least one processor and at least one storage device. The method may include obtaining image data of a subject to be scanned by a medical device. The method may include determining a scan range of the subject based on the image data. The scan range may include at least one scan area of the subject. The method may include determining at least one parameter value of at least one scan parameter based on the at least one scan area of the subject.

In some embodiments, the image data of the subject may be obtained by an image capturing device or the medical device.

In some embodiments, the method may include identifying the at least one scan area of the subject based on the image data of the subject using an identification model. The method may include determining the scan range of the subject based on the at least one scan area of the subject.

In some embodiments, the method may include obtaining element information associated with at least one element of the image data. The method may include identifying the at least one scan area of the subject based on the element information. The method may include determining the scan range of the subject based on the at least one scan area of the subject.

In some embodiments, the method may include, for each scan area of the at least one scan area, obtaining a relationship between a scan area and at least one scan parameter. The method may include determining the at least one parameter value of the at least one scan parameter based on the scan area and the relationship.

In some embodiments, the method may include identifying at least one feature point in the image data. The method may include determining a target position of the subject based on the at least one feature point. The method may include causing the medical device to move the subject to the target position.

In some embodiments, the method may include causing the medical device to scan the subject based on the scan range and the at least one parameter value of the at least one scan parameter.

In some embodiments, the method may include generating an image of the subject based on the scan of the subject by the medical device. The method may include adjusting the at least one parameter value of the at least one scan parameter based on the image.

In some embodiments, the method may include determining at least one reconstruction parameter corresponding to the at least one scan area of the subject. The method may include generating an image of the subject based on the scan of the subject by the medical device and the at least one reconstruction parameter.

In some embodiments, the scan of the subject may be a computed tomography (CT) scan or a magnetic resonance imaging (MRI) scan. The image of the subject may be a CT image or an MRI image. The method may include obtaining PET scan data by performing, based on the scan range, a PET scan of the subject using a PET device. The method may include performing an attenuation correction on the PET scan data based on the CT image or the MRI image.

In some embodiments, the method may include determining posture information of the subject based on the image data. The method may include applying the posture information to a scan protocol of the subject.

In some embodiments, the method may include obtaining the scan protocol of the subject. The method may include determining whether the scan protocol includes preset posture information.

In some embodiments, the method may include, in response to determining that the scan protocol does not include the preset posture information, storing the posture information in the scan protocol.

In some embodiments, the method may include, in response to determining that the scan protocol includes the preset posture information, updating the preset posture information based on the posture information.

In some embodiments, the method may include causing a voice processing device to transmit the posture information to a user. The method may include causing a terminal device to display the posture information to the user.

In some embodiments, the method may include obtaining, via the terminal device or the voice processing device, an input relating to the posture information of the subject from the user. The method may include updating the posture information of the subject based on the input.

In some embodiments, the method may include comparing the posture information of the subject and the input of the user to generate a comparison result. The method may include updating the posture information of the subject based on the comparison result.

According to another aspect of the present disclosure, a method may be implemented on a computing device having at least one processor and at least one storage device. The method may include obtaining image data of a subject to be scanned by a medical device. The method may include determining posture information of the subject based on the image data. The method may include applying the posture information to a scan protocol of the subject.

In some embodiments, the method may include obtaining the scan protocol of the subject. The method may include determining whether the scan protocol includes preset posture information. The method may include, in response to determining that the scan protocol does not include the preset posture information, storing the posture information in the scan protocol. The method may include, in response to determining that the scan protocol includes the preset posture information, updating the preset posture information based on the posture information.

According to another aspect of the present disclosure, a system may include at least one storage device storing a set of instructions, and at least one processor in communication with the at least one storage device. When executing the stored set of instructions, the at least one processor causes the system to perform a method. The method may include obtaining image data of a subject to be scanned by a medical device. The method may include determining a scan range of the subject based on the image data. The scan range may include at least one scan area of the subject. The method may include determining at least one parameter value of at least one scan parameter based on the at least one scan area of the subject.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
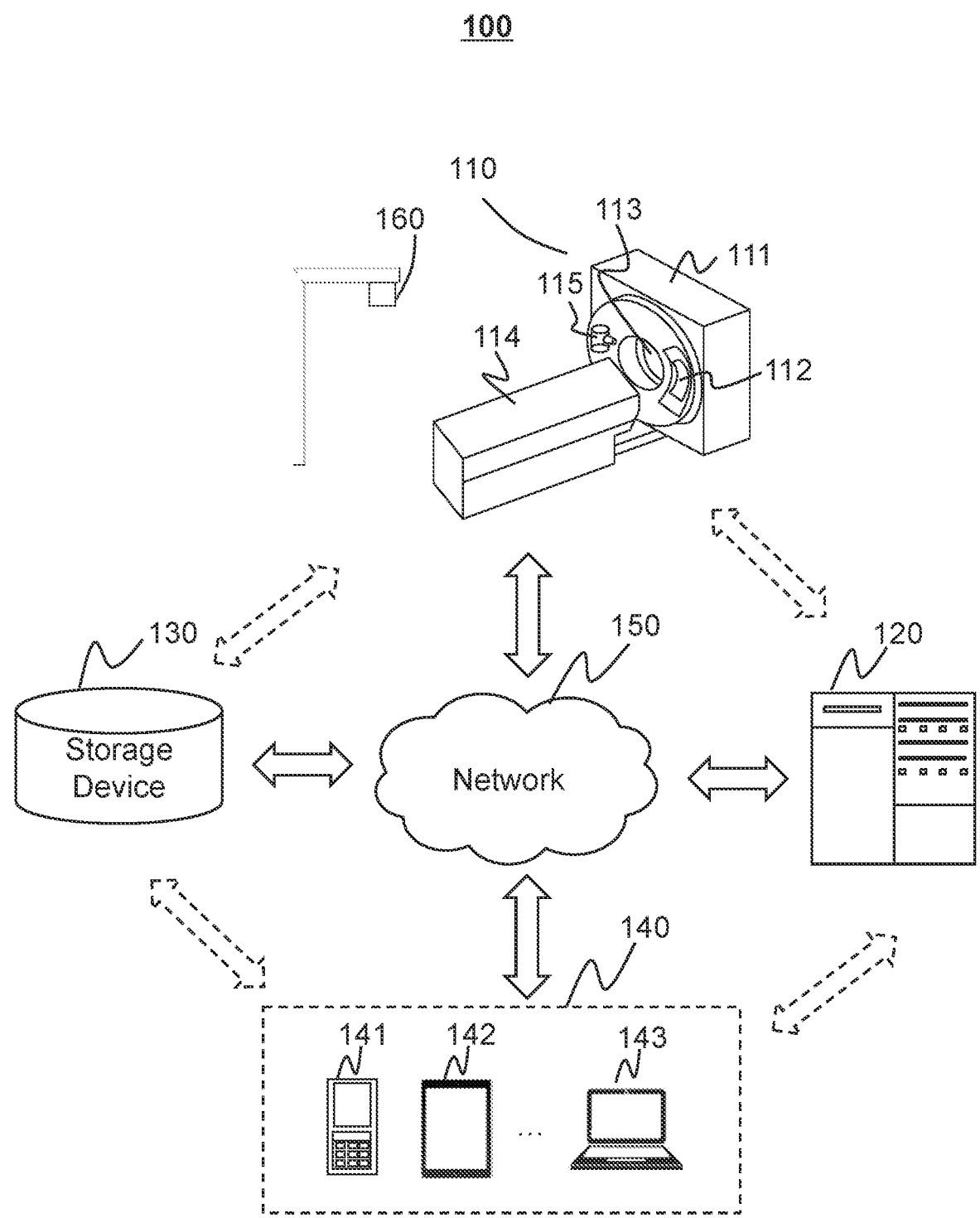
FIG. 1 is a schematic diagram illustrating an exemplary medical system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Also, the term "exemplary" is intended to refer to an example or illustration.

It will be understood that the terms "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be capable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

Spatial and functional relationships between elements are described using various terms, including "connected," "attached," and "mounted." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, attached, or positioned to another element, there are no intervening elements present. Other words used to describe the relationship between elements should be interpreted in a like fashion (e.g., "between," versus "directly between," "adjacent," versus "directly adjacent," etc.).

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. The term "anatomical structure" in the present disclosure may refer to gas (e.g., aft), liquid (e.g., water), solid (e.g., stone), cell, tissue, organ of a subject, or any combination thereof, which may be displayed in an image and really exist in or on the subject's body. The term "region," "location," and "area" in the present disclosure may refer to a location of an anatomical structure shown in the image or an actual location of the anatomical structure existing in or on the subject's body, since the image may indicate the actual location of a certain anatomical structure existing in or on the subject's body. The term "an image of a subject" may be referred to as the subject for brevity.

An aspect of the present disclosure relates to systems and methods for determining a scan parameter of a subject. According to some embodiments of the present disclosure, a processing device may obtain image data of a subject to be scanned by a medical device. The processing device may determine a scan range of the subject based on the image data. The scan range may include at least one scan area of the subject. The processing device may determine at least one parameter value of at least one scan parameter based on the at least one scan area of the subject. In some embodiments, the processing device may determine posture information of the subject based on the image data. The processing device may determine the scan range of the subject based on the image data and the posture information.

Accordingly, one or more scan areas of a subject may be determined based on image data of the subject. In addition, parameter value(s) of scan parameter(s) corresponding to each scan area of the one or more scan areas may further be determined. The systems and methods disclosed herein for scan parameter determination for different scan areas may be implemented with reduced or minimal or without user intervention. A plurality of scan areas of the subject may be imaged in one scan using different sets of parameter value(s) of scan parameter(s). Compared with conventional ways, the systems and methods disclosed herein are more efficient and accurate by, e.g., reducing the workload of a user, cross-user variations, and the time needed for the scan.

Another aspect of the present disclosure relates to systems and methods for determining posture information of a subject. According to some embodiments of the present disclosure, a processing device may obtain image data of a subject to be scanned by a medical device. The processing device may determine posture information of the subject based on the image data. The processing device may store the posture information in a scan protocol of the subject.

Accordingly, posture information of a subject may be determined based on image data, and the posture information may be applied to a scan protocol of the subject. Traditionally, a user (e.g., an operator, a doctor) may instruct a subject to take and maintain a particular posture during the scan, and manually input the posture, such as choosing and executing a scan protocol particularly designed for that posture. When the subject changes his/her posture during the scan, such as mandated by the diagnosis or the subject's health condition, the user may need to manually update the posture. Thus, the manual posture information determination procedure often involves a lot of human intervention, and sometimes consumes a considerable amount of time, causing substantial delay and subject discomfort. Compared with conventional ways, the automated posture information determination systems and methods disclosed herein may be more accurate and efficient by, e.g., reducing the workload of a user, cross-user variations, and the time needed for the selection of the posture information of the subject.

FIG. 1 is a schematic diagram illustrating an exemplary medical system according to some embodiments of the present disclosure. As illustrated, a medical system 100 may include a medical device 110, a processing device 120, a storage device 130, one or more terminals 140, a network 150, and an image capturing device 160. In some embodiments, the medical device 110, the processing device 120, the storage device 130, the terminal(s) 140, and/or the image capturing device 160 may be connected to and/or communicate with each other via a wireless connection, a wired connection, or a combination thereof. The connection between the components of the medical system 100 may be variable. Merely by way of example, as illustrated in FIG. 1, the medical device 110 may be connected to the processing device 120 directly as indicated by the bi-directional arrow in dotted lines linking the medical device 110 and the processing device 120, or through the network 150. As another example, the storage device 130 may be connected to the medical device 110 directly as indicated by the bi-directional arrow in dotted lines linking the medical device 110 and the storage device 130, or through the network 150. As still another example, the terminal 140 may be connected to the processing device 120 directly as indicated by the bi-directional arrow in dotted lines linking the terminal 140 and the processing device 120, or through the network 150. As still another example, the terminal 140 may be connected to the storage device 130 directly as indicated by the bi-directional arrow in dotted lines linking the terminal 140 and the storage device 130, or through the network 150.

The medical device 110 may generate or provide medical image data related to a subject via scanning the subject. In some embodiments, the subject may include a biological subject and/or a non-biological subject. For example, the subject may include a specific portion of a body, such as the head, the thorax, the abdomen, or the like, or a combination thereof. As another example, the subject may be a man-made composition of organic and/or inorganic matters that are with or without life. In some embodiments, the medical system 100 may include modules and/or components for performing imaging, treatment, and/or related analysis. In some embodiments, the medical image data relating to the subject may include projection data, one or more images of the subject, etc. The projection data may include raw data generated by the medical device 110 by scanning the subject and/or data generated by a forward projection on an image of the subject.

In some embodiments, the medical device 110 may be a non-invasive biomedical medical imaging device for disease diagnostic or research purposes. The medical device 110 may include a single modality scanner and/or a multi-modality scanner. The single modality scanner may include, for example, an ultrasound scanner, an X-ray scanner, an computed tomography (CT) scanner, a magnetic resonance imaging (MRI) scanner, an ultrasonography scanner, a positron emission tomography (PET) scanner, an optical coherence tomography (OCT) scanner, an ultrasound (US) scanner, an intravascular ultrasound (IVUS) scanner, a near infrared spectroscopy (NIRS) scanner, a far infrared (FIR) scanner, or the like, or any combination thereof. The multi-modality scanner may include, for example, an X-ray imaging-magnetic resonance imaging (X-ray-MRI) scanner, a positron emission tomography-X-ray imaging (PET-X-ray) scanner, a single photon emission computed tomography-magnetic resonance imaging (SPECT-MRI) scanner, a positron emission tomography-computed tomography (PET-CT) scanner, a digital subtraction angiography-magnetic resonance imaging (DSA-MRI) scanner, etc. It should be noted that the scanner described above is merely provided for illustration purposes, and not intended to limit the scope of the present disclosure. The term "imaging modality" or "modality" as used herein broadly refers to an imaging method or technology that gathers, generates, processes, and/or analyzes imaging information of a subject.

For illustration purposes, the present disclosure mainly describes systems and methods relating to CT system. It should be noted that the CT system described below is merely provided as an example, and not intended to limit the scope of the present disclosure. The systems and methods disclosed herein may be applied to any other medical systems.

In some embodiments, the medical device 110 may include a gantry 111, a detector 112, a detection region 113, a scanning table 114, and a radiation source 115. The gantry 111 may support the detector 112 and the radiation source 115. The subject may be placed on the scanning table 114 and moved into the detection region 113 to be scanned. The radiation source 115 may emit radioactive rays to the subject. The radioactive rays may include a particle ray, a photon ray, or the like, or a combination thereof. In some embodiments, the radioactive rays may include a plurality of radiation particles (e.g., neutrons, protons, electron, μ-mesons, heavy ions), a plurality of radiation photons (e.g., X-ray, γ-ray, ultraviolet, laser), or the like, or a combination thereof. In some embodiments, the radiation source 115 may include a tube (not shown in FIG. 1) and a collimator (not shown in FIG. 1). The tube may generate and/or emit radiation beams travelling toward the subject. In some embodiments, the tube may include an anode target (not shown in FIG. 1) and a filament (not shown in FIG. 1). The filament may be configured to generate electrons to bombard the anode target. The anode target may be configured to generate the radiation rays (e.g., X-rays) when the electrons bombard the anode target. The collimator may be configured to control the irradiation region (i.e., a radiation field) on the subject.

The detector 112 may detect radiation and/or a radiation event (e.g., gamma photons) emitted from the detection region 113. In some embodiments, the detector 112 may include a plurality of detector units. The detector units may include a scintillation detector (e.g., a cesium iodide detector) or a gas detector. The detector unit may be a single-row detector or a multi-rows detector.

In some embodiments, the medical device 110 may further include a treatment component (not shown in FIG. 1). The treatment component may include a device or apparatus that is capable of providing treatment beams (e.g., radiation rays). In some embodiments, the treatment component may include a treatment radiation source (not shown in FIG. 1). In some embodiments, the treatment radiation source may be a linear accelerator (LINAC) that accelerates electrons and generates radiation rays thereby. In some embodiments, the radiation source 115 and the treatment radiation source may be integrated as one radiation source to image and/or treat the subject. In some embodiments, the treatment radiation source may be used as the radiation source 115 to image and/or treat the subject. In some embodiments, the medical device 110 may be located in an examination room (e.g., a shielded room) to prevent radiation rays from leaking to the outdoors.

The processing device 120 may process data and/or information obtained from the medical device 110, the storage device 130, the image capturing device 160, and/or the terminals) 140. For example, the processing device 120 may obtain image data of a subject. As another example, the processing device 120 may determine a scan range of a subject based on image data. As another example, the processing device 120 may determine at least one parameter value of at least one scan parameter based on at least one scan area of a subject. As still another example, the processing device 120 may determine posture information of a subject based on image data. As still another example, the processing device 120 may store posture information in a scan protocol of a subject.

In some embodiments, the processing device 120 may be a single server or a server group. The server group may be centralized or distributed. In some embodiments, the processing device 120 may be local or remote. For example, the processing device 120 may access information and/or data from the medical device 110, the storage device 130, the image capturing device 160, and/or the terminal(s) 140 via the network 150. As another example, the processing device 120 may be directly connected to the medical device 110, the terminal(s) 140, the image capturing device 160, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be part of the terminal 140. In some embodiments, the processing device 120 may be part of the medical device 110. In some embodiments, the processing device 120 may be part of the image capturing device 160.

The storage device 130 may store data, instructions, and/or any other information. In some embodiments, the storage device 130 may store data obtained from the medical device 110, the processing device 120, the image capturing device 160, and/or the terminal(s) 140. The data may include image data acquired by the processing device 120, algorithms and/or models for processing the image data, etc. For example, the storage device 130 may store image data of a subject obtained from a medical device (e.g., the medical device 110) or an image capturing device (e.g., the image capturing device 160). As another example, the storage device 130 may store a scan range of a subject determined by the processing device 120. As still another example, the storage device 130 may store at least one parameter value of at least one scan parameter determined by the processing device 120. As still another example, the storage device 130 may store posture information of a subject determined by the processing device 120. As still another example, the storage device 130 may store a scan protocol (e.g., a digital imaging and communications in medicine (DICOM)) of a subject. In some embodiments, the storage device 130 may store data and/or instructions that the processing device 120, the image capturing device 160, and/or the terminal 140 may execute or use to perform exemplary methods described in the present disclosure. In some embodiments, the storage device 130 may include a mass storage, removable storage, a volatile read-and-write memory, a read-only memory (ROM), or the like, or any combination thereof. Exemplary mass storages may include a magnetic disk, an optical disk, a solid-state drive, etc. Exemplary removable storages may include a flash drive, a floppy disk, an optical disk, a memory card, a zip disk, a magnetic tape, etc. Exemplary volatile read-and-write memories may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the medical system 100 (e.g., the processing device 120, the terminal(s) 140). One or more components in the medical system 100 may access the data or instructions stored in the storage device 130 via the network 150. In some embodiments, the storage device 130 may be integrated into the medical device 110, the terminal(s) 140, or the image capturing device 160.

The terminal(s) 140 may be connected to and/or communicate with the medical device 110, the processing device 120, and/or the storage device 130. In some embodiments, the terminal 140 may include a mobile device 141, a tablet computer 142, a laptop computer 143, or the like, or any combination thereof. For example, the mobile device 141 may include a mobile phone, a personal digital assistant (PDA), a gaming device, a navigation device, a point of sale (POS) device, a laptop, a tablet computer, a desktop, or the like, or any combination thereof. In some embodiments, the terminal 140 may include an input device, an output device, etc. The input device may include alphanumeric and other keys that may be input via a keyboard, a touchscreen (for example, with haptics or tactile feedback), a speech input, an eye tracking input, a brain monitoring system, or any other comparable input mechanism. Other types of the input device may include a cursor control device, such as a mouse, a trackball, or cursor direction keys, etc. The output device may include a display, a printer, or the like, or any combination thereof.

The network 150 may include any suitable network that can facilitate the exchange of information and/or data for the medical system 100. In some embodiments, one or more components of the medical system 100 (e.g., the medical device 110, the processing device 120, the storage device 130, the terminal(s) 140, the image capturing device 160, etc.) may communicate information and/or data with one or more other components of the medical system 100 via the network 150. For example, the processing device 120 and/or the terminal 140 may obtain image data from the medical device 110 via the network 150. As another example, the processing device 120 and/or the terminal 140 may obtain information stored in the storage device 130 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the medical system 100 may be connected to the network 150 to exchange data and/or information.

The image capturing device 160 may be configured to capture image data of a subject before, during, and/or after the medical device 110 performs a scan on the subject. The image capturing device 160 may be and/or include any suitable device that is capable of capturing image data of the subject. For example, the image capturing device 160 may include a camera (e.g., a digital camera, an analog camera, etc.), a red-green-blue (RGB) sensor, an RGB-depth (RGB-D) sensor, or another device that can capture color image data of the subject. As another example, the image capturing device 160 may be used to acquire point-cloud data of the subject. The point-cloud data may include a plurality of data points, each of which may represent a physical point on a body surface of the subject and can be described using one or more feature values of the physical point (e.g., feature values relating to the position and/or the composition of the physical point). Exemplary image capturing devices 160 capable of acquiring point-cloud data may include a 3D scanner, such as a 3D laser imaging device, a structured light scanner (e.g., a structured light laser scanner). Merely by way of example, a structured light scanner may be used to execute a scan on the subject to acquire the point cloud data. During the scan, the structured light scanner may project structured light (e.g., a structured light spot, a structured light grid) that has a certain pattern toward the subject. The point-cloud data may be acquired according to the structure light projected on the subject. As yet another example, the image capturing device 160 may be used to acquire depth image data of the subject. The depth image data may refer to image data that includes depth information of each physical point on the body surface of the subject, such as a distance from each physical point to a specific point (e.g., an optical center of the image capturing device 160). The depth image data may be captured by a range sensing device, e.g., a structured light scanner, a time-of-flight (TOF) device, a stereo triangulation camera, a sheet of light triangulation device, an interferometry device, a coded aperture device, a stereo matching device, or the like, or any combination thereof.

In some embodiments, the image capturing device 160 may be a device independent from the medical device 110 as shown in FIG. 1. For example, the image capturing device 160 may be a camera mounted on the ceiling in an examination/treatment room where the medical device 110 is located. In some embodiments, the image capturing device 160 may be integrated into or mounted on the medical device 110 (e.g., the gantry 111). For example, the image capturing device 160 may be mounted on the housing of the gantry 111 (e.g., a position of the housing directly above the scanning table 114) of the medical device 110 to record the front view of the subject on the scanning table 114. As another example, the image capturing device 160 may be mounted on the side of the gantry 111 of the medical device 110 to record the side view of the subject on the scanning table 114. As still another example, a plurality of image capturing devices 160 may be mounted on different positions of the gantry 111 to record a perspective view of the subject on the scanning table 114.

In some embodiments, the mounting location of the image capturing device 160 may be determined based on a capture range of the image capturing device 160 and feature information (e.g., a location, a length, a width, a height) of the scanning table 114. For example, the image capturing device 160 may be mounted at a specific location such that the capture range of the image capturing device 160 can cover the entire range of the scanning table 114.

For instance, the image capturing device 160 is mounted in the detection region 113 (e.g., on the gantry 111) of the medical device 110; the image capturing device 160 may capture the image data of the subject when the subject on the scanning table 114 is located at a target position (e.g., a scan start position) in the detection region 113. As another example, the image capturing device 160 is mounted outside the detection region 113 of the medical device 110 (e.g., on the ceiling in an examination room); the image capturing device 160 may capture the image data of the subject before the subject on the scanning table 114 moves into the detection region 113.

In some embodiments, the image data acquired by the image capturing device 160 may be transmitted to the processing device 120 for further analysis. In some embodiments, the image data acquired by the image capturing device 160 may be transmitted to a terminal device (e.g., the terminal(s) 140) for display and/or a storage device (e.g., the storage device 130) for storage. Additionally or alternatively, the image capturing device 160 may process the image data to generate a processing result (e.g., posture information, a scan range), and transmit the processing result to one or ore components (e.g., the processing device 120) of the medical system 100.

In some embodiments, the image capturing device 160 may capture the image data of the subject continuously or intermittently (e.g., periodically) before, during, and/or after the scan of the subject performed by the medical device 110. In some embodiments, the acquisition of the image data by the image capturing device 160, the transmission of the captured image data to the processing device 120, and the analysis of the image data may be performed substantially in real time so that the image data may provide information indicating a substantially real time status of the subject.

In some embodiments, the medical system 100 may further include a voice processing device (not shown in FIG. 1). In some embodiments, the voice processing device may include a speaker, a microphone, an integrated device including the speaker and the microphone, or the like, or any combination thereof. The speaker may convert an electrical signal into a voice. The microphone may be a transducer that converts a voice into an electrical signal.

In some embodiments, the voice processing device may include a voice recognition module configured to recognize information provided in the form of an audio. For example, the voice processing device may obtain instructions provide by an audio input from a user (e.g., a doctor, an operator), and convert the audio input to information in the form of, e.g., text. The voice processing device may further cause the terminal device 140 to display the converted information. As another example, the voice processing device may include a voice collection button. A user may press the voice collection button to provide an audio input.

In some embodiments, the voice processing device may broadcast information displayed on the terminal device 140 (or referred to as display information for brevity). The display information may include posture information of the subject, one or more scan areas of the subject, one or more scan parameters, or the like, or any combination thereof. For example, the voice processing device may obtain posture information of the subject from the terminal device 140, and broadcast the posture information to a user (e.g., a doctor, an operator) of the medical system 100.

In some embodiments, the voice processing device may be a device independent from the medical device 110 and/or the terminal device 140. For example, the voice processing device may include a speaker or a microphone mounted on the ceiling or a wall in an examination/treatment room where the medical device 110 is located. In some embodiments, the voice processing device may be integrated into or mounted on the medical device 110 and/or the terminal device 140. For example, the voice processing device may be mounted on a location of the medical device 110 close to a user to ensure an accurate acquisition of voice information from the user.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure. In some embodiments, the medical system 100 may include one or more additional components and/or one or more components of the medical system 100 described above may be omitted. Additionally or alternatively, two or more components of the medical system 100 may be integrated into a single component. A component of the medical system 100 may be implemented on two or more sub-components.

Figure 2:
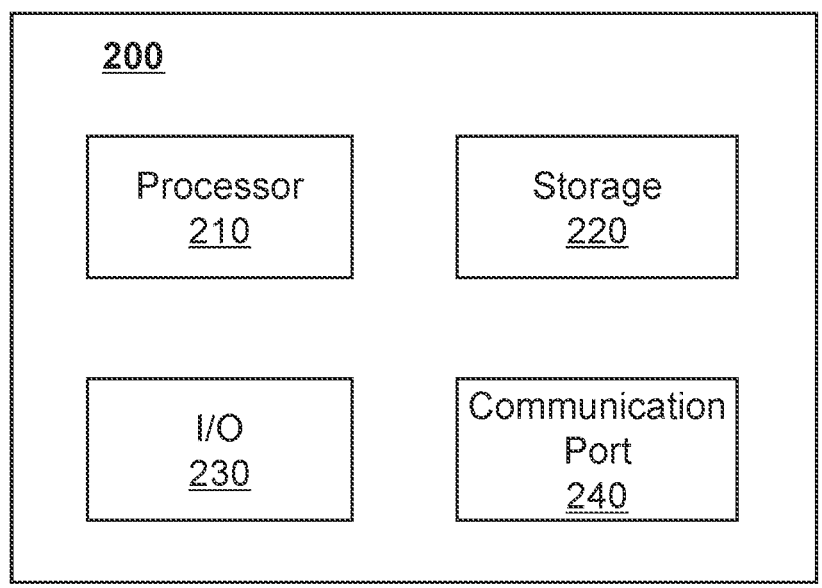
FIG. 2 is a schematic diagram illustrating exemplary hardware and/or software components of an exemplary computing device on which the processing device 120 may be implemented according to some embodiments of the present disclosure.

FIG. 2 is a schematic diagram illustrating exemplary hardware and/or software components of an exemplary computing device 200 on which the processing device 120 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 210 may process image data obtained from the medical device 110, the terminals) 140, the storage device 130, and/or any other component of the medical system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combination thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the medical device 110, the terminal(s) 140, the storage device 130, and/or any other component of the medical system 100. The storage 220 may be similar to the storage device 130 described in connection with FIG. 1, and the detailed descriptions are not repeated here.

The I/O 230 may input and/or output signals, data, information, etc. In some embodiments, the I/O 230 may enable a user interaction with the processing device 120. In some embodiments, the I/O 230 may include an input device and an output device. Examples of the input device may include a keyboard, a mouse, a touchscreen, a microphone, a sound recording device, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touchscreen, or the like, or a combination thereof.

The communication port 240 may be connected to a network (e.g., the network 150) to facilitate data communications. The communication port 240 may establish connections between the processing device 120 and the medical device 110, the terminal(s) 140, and/or the storage device 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. In some embodiments, the communication port 240 may be and/or include a standardized communication port, such as RS232, RS485. In some embodiments, the communication port 240 may be a specially designed communication port. For example, the communication port 240 may be designed in accordance with the digital imaging and communications in medicine (DICOM) protocol.

Figure 3:
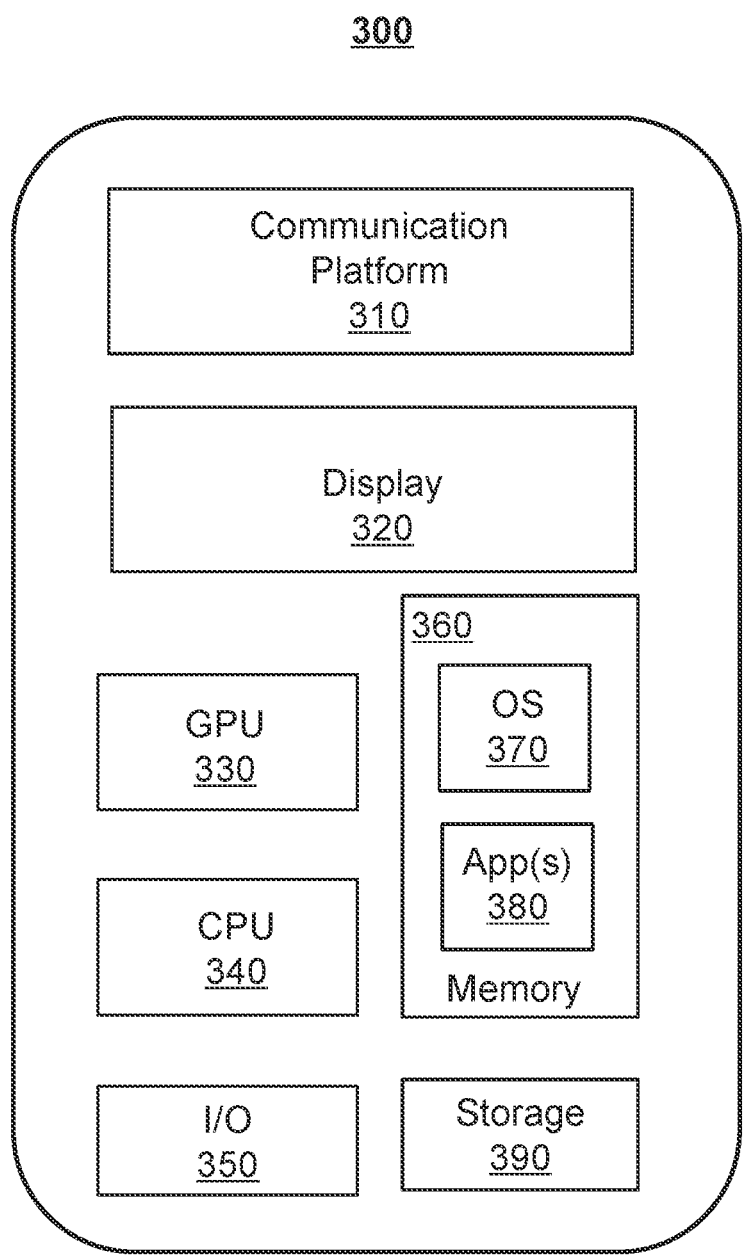
FIG. 3 is a schematic diagram illustrating exemplary hardware and/or software components of an exemplary mobile device 300 according to some embodiments of the present disclosure.

FIG. 3 is a schematic diagram illustrating exemplary hardware and/or software components of an exemplary mobile device 300 according to some embodiments of the present disclosure. In some embodiments, the terminal(s) 140 and/or the processing device 120 may be implemented on a mobile device 300, respectively.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300.

In some embodiments, the communication platform 310 may be configured to establish a connection between the mobile device 300 and other components of the medical system 100, and enable data and/or signal to be transmitted between the mobile device 300 and other components of the medical system 100. For example, the communication platform 310 may establish a wireless connection between the mobile device 300 and the medical device 110, and/or the processing device 120. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. The communication platform 310 may also enable the data and/or signal between the mobile device 300 and other components of the medical system 100. For example, the communication platform 310 may transmit data and/or signals inputted by a user to other components of the medical system 100. The inputted data and/or signals may include a user instruction. As another example, the communication platform 310 may receive data and/or signals transmitted from the processing device 120. The received data and/or signals may include imaging data acquired by a detector of the medical device 110.

In some embodiments, a mobile operating system (OS) 370 (e.g., iOS™, Android™ Windows Phone™, etc.) and one or more applications (App(s)) 380 may be loaded into the memory 360 from the storage 390 in order to be executed by the CPU 340. The applications 380 may include a browser or any other suitable mobile apps for receiving and rendering information from the processing device 120. User interactions with the information stream may be achieved via the I/O 350 and provided to the processing device 120 and/or other components of the medical system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 4:
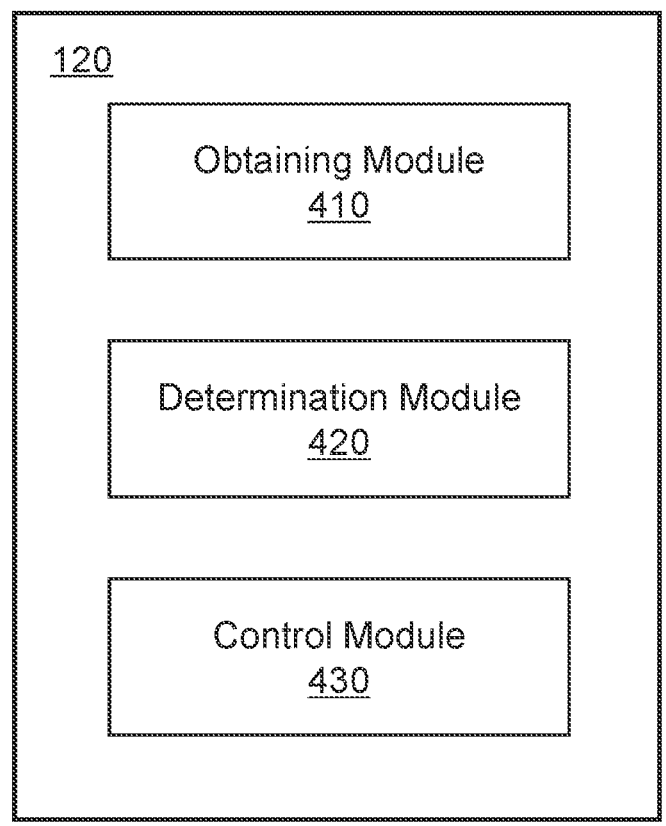
FIG. 4 is a block diagram illustrating an exemplary processing device according to some embodiments of the present disclosure.

FIG. 4 is a block diagram illustrating an exemplary processing device according to some embodiments of the present disclosure. In some embodiments, the processing device 120 may include an obtaining module 410, a determination module 420, and a control module 430.

The obtaining module 410 may be configured to obtain data and/or information associated with the medical system 100. The data and/or information associated with the medical system 100 may include image data of a subject to be scanned by a medical device, a scan range of the subject, at least one parameter value of at least one scan parameter of the subject, posture information of the subject, a scan protocol of the subject, or the like, or any combination thereof. For example, the obtaining module 410 may obtain image data of a subject. As another example, the obtaining module 410 may obtain a scan protocol of a subject. In some embodiments, the obtaining module 410 may obtain the data and/or the information associated with the medical system 100 from one or more components (e.g., the medical device 110, the storage device 130, the terminal 140) of the medical system 100 via the network 150.

The determination module 420 may be configured to determine data and/or information associated with the medical system 100. For example, the determination module 420 may determine a scan range of a subject based on image data (and posture information of a subject). As another example, the determination module 420 may determine at least one parameter value of at least one scan parameter based on at least one scan area of a subject. As still another example, the determination module 420 may determine posture information of a subject based on image data. As still another example, the determination module 420 may apply posture information to a scan protocol of a subject.

The control module 430 may be configured to control one or more components (e.g., the medical device 110) of the medical system 100. For example, the control module 430 may cause a medical device to scan a subject based on scan range and at least one parameter value of at least one scan parameter.

It should be noted that the above description of the processing device 120 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more modules may be added or omitted in the processing device 120. For example, the processing device 120 may further include a storage module (not shown in FIG. 4) configured to store data and/or information (e.g., image data, a scan range, a scan parameter, posture information) associated with the medical system 100.

Figure 5:
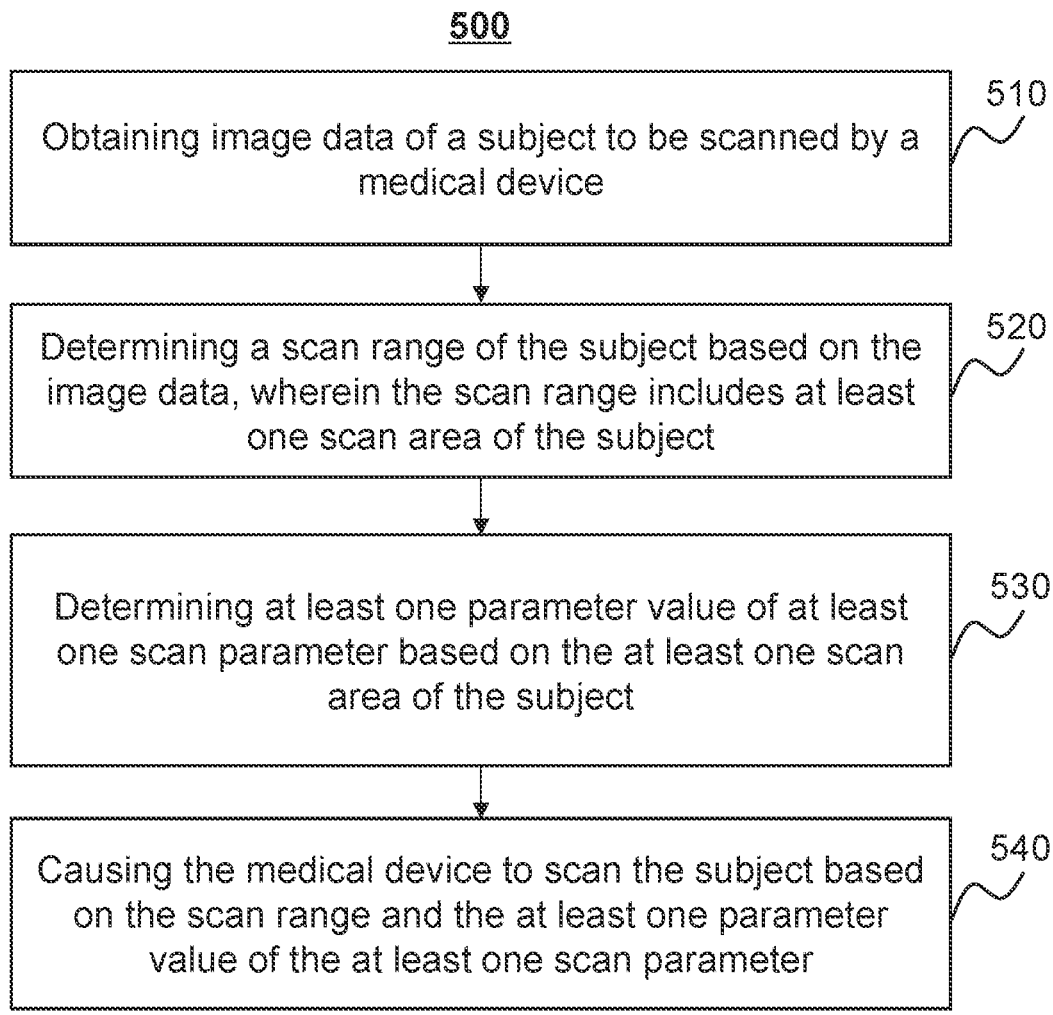
FIG. 5 is a flowchart illustrating an exemplary process for determining at least one parameter value of at least one scan parameter according to some embodiments of the present disclosure.

FIG. 5 is a flowchart illustrating an exemplary process for determining at least one parameter value of at least one scan parameter according to some embodiments of the present disclosure. In some embodiments, the process 500 may be implemented in the medical system 100 illustrated in FIG. 1. For example, the process 500 may be stored in the storage device 130 and/or the storage (e.g., the storage 220, the storage 390) as a form of instructions, and invoked and/or executed by the processing device 120 (e.g., the processor 210 of the computing device 200 as illustrated in FIG. 2, the CPU 340 of the mobile device 300 as illustrated in FIG. 3). The operations of the illustrated process presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

In 510, the processing device 120 (e.g., the obtaining module 410) may obtain image data of a subject to be scanned by a medical device (e.g., the medical device 110).

In some embodiments, the subject may be a biological subject (e.g., a patient) and/or a non-biological subject to be scanned (e.g., imaged or treated) by the medical device (e.g., the medical device 110). The image data of the subject refers to image data corresponding to the entire subject or image data corresponding to a portion of the subject. In some embodiments, the image data of the subject may include a two-dimensional (2D) image, a three-dimensional (3D) image, a four-dimensional (4D) image (e.g., a series of 3D images over time), and/or any related image data. In some embodiments, the image data of the subject may include color image data, point-cloud data, depth image data, mesh data, scan data, projection data, or the like, or any combination thereof, of the subject.

In some embodiments, the image data of the subject may be captured by an image capturing device (e.g., the image capturing device 160), the medical device, or a second medical device. The type of the second medical device may be the same as or different from that of the medical device. For example, both the medical device and the second medical device may be CT devices. As another example, the medical device may be a CT device, and the second medical device may be a PET device.

For example, the image data may be obtained by a PET device (or a SPECT device). A relatively low dose of PET tracer (or a SPECT tracer) may be injected into the subject. After the subject on a scanning table (e.g., the scanning table 114) moves into a detection region (e.g., the detection region 113) of the PET device, the PET device may perform a scan on the subject to obtain PET projection data. The image data (e.g., a PET image) of the subject may be reconstructed based on the PET projection data using a PET image reconstruction technique. As another example, the image data may be obtained by a CT device. After the subject on the scanning table (e.g., the scanning table 114) moves into a detection region (e.g., the detection region 113) of the CT device, a radiation source (e.g., e.g., the radiation source 115) of the CT device may emit X-rays of a relatively low dose to the subject, and a detector (e.g., the detector 112) of the CT device may detect X-rays passing through the subject, to generate CT projection data. The image data (e.g., a CT image) of the subject may be reconstructed based on the CT projection data using a CT image reconstruction technique. Accordingly, the image data of the subject may be obtained via the medical device by performing a low-dose scan on the subject, which may avoid unnecessary radiation to the subject, reduce the time needed for the scan, and simplify the scan process.

In some embodiments, the processing device 120 may obtain the image data from the image capturing device, the medical device, or the second medical device. Alternatively, the image data may be acquired by the image capturing device, the medical device, or the second medical device, and stored in a storage device (e.g., the storage device 130, the storage 220, the storage 390, or an external source). The processing device 120 may retrieve the image data from the storage device.

In some embodiments, the image data may be original image data captured by the image capturing device, the medical device, or the second medical device. Alternatively, the image data may be determined by processing the original data. For example, the processing device 120 may perform a denoising operation on the original image data to generate denoised image data, and determine the denoised image data as the image data of the subject. As another example, the processing device 120 may perform a gray-scale processing operation on the original image data to generate processed image data. As a further example, the processing device 120 may extract a contour of the subject in the processed image data using an image gradient algorithm, and determine the contour of the subject as the image data of the subject.

In 520, the processing device 120 (e.g., the determination module 420) may determine a scan range of the subject based on the image data.

In some embodiments, the scan range may be defined by a scan start position, a scan center position, a scan end position, or the like, or any combination thereof. In some embodiments, the scan range may correspond to at least one scan area of the subject. As used herein, a scan area of a subject refers to a desired portion (e.g., a specific organ or tissue) of the subject to be scanned (imaged or treated) by the medical device. For illustration purposes, if the scan areas of the subject include the right thigh, the right knee, and the right calf of the subject, the scan start position may be determined as the right hip of the subject, and the scan end position may be determined as the right ankle of the subject.

In some embodiments, the processing device 120 may identify the at least one scan area of the subject based on the image data of the subject. The processing device 120 may further determine the scan range of the subject based on the at least one scan area of the subject. For example, the processing device 120 may identify the at least one scan area of the subject based on the image data of the subject using an artificial intelligence (AI) technology (e.g., a computer vision). As used herein, a computer vision refers to an interdisciplinary scientific field that deals with how computers can gain high-level understanding from digital images or videos. Computer vision tasks may include methods for acquiring, processing, analyzing, and understanding digital images, and extraction of high-dimensional data from the real world in order to produce numerical or symbolic information, e.g., in the form of decisions.

Merely by way of example, the processing device 120 may identify the at least one scan area of the subject based on the image data of the subject using an identification model. The identification model refers to a mod& (e.g., a machine learning model) or an algorithm for determining one or more regions of a subject based on image data of the subject. For example, the processing device 120 may input the image data of the subject into the identification model, and the identification model may output identification of the one or more regions of the subject by processing the image data. The identification of a region of the subject may be presented by delineating an outline or contour of the region. Alternatively, the processing device 120 may determine posture information of the subject based on the image data as described elsewhere in the present disclosure (e.g., FIG. 6 and descriptions thereof). The processing device 120 may identify the at least one scan area of the subject based on the image data of the subject and posture information of the subject using the identification model. For example, the processing device 120 may input the image data of the subject and the posture information of the subject into the identification model, and the identification mod& may output identification of the one or more regions of the subject by processing the image data.

In some embodiments, the identification model may be obtained by training a preliminary model using a plurality of groups of training samples. In some embodiments, the identification model may be predetermined by a computing device (e.g., the processing device 120 or a computing device of a vendor of the identification model) and stored in a storage device (e.g., the storage device 130, the storage 220, the storage 390, or an external source). The processing device 120 may obtain the identification mod& from the storage device. Alternatively, the processing device 120 may determine the identification model by performing a training.

To train an identification model, a plurality of groups of training samples may be used. A group of the plurality of groups of training samples may include sample image data of a sample subject and sample region(s) of the sample subject corresponding to the sample image data. In some embodiments, the preliminary model may be of any type of machine learning model. Merely by way of example, the preliminary model may include an artificial neural network (ANN), a random forest model, a support vector machine, a decision tree, a convolutional neural network (CNN), a Recurrent Neural Network (RNN), a deep learning model, a Bayesian network, a K-nearest neighbor (KNN) model, a generative adversarial network (GAN) model, etc. The training of the preliminary model may be implemented according to a machine learning algorithm, such as an artificial neural network algorithm, a deep learning algorithm, a decision tree algorithm, an association rule algorithm, an inductive logic programming algorithm, a support vector machine algorithm, a clustering algorithm, a Bayesian network algorithm, a reinforcement learning algorithm, a representation learning algorithm, a similarity and metric learning algorithm, a sparse dictionary learning algorithm, a genetic algorithm, a rule-based machine learning algorithm, or the like, or any combination thereof. The machine learning algorithm used to generate the identification model may be a supervised learning algorithm, a semi-supervised learning algorithm, an unsupervised learning algorithm, or the like.

In some embodiments, the identification model may be determined by performing a plurality of iterations to iteratively update one or more parameter values of the preliminary model. For each of the plurality of iterations, a specific group of training samples may first be input into the preliminary model. For example, specific sample image data in a specific group of training samples may be inputted into an input layer of the preliminary model, and a sample body region corresponding to the specific sample image data may be inputted into an output layer of the preliminary model as a desired output of the preliminary model. The preliminary model may extract one or more image features (e.g., a low-level feature (e.g., an edge feature, a texture feature), a high-level feature (e.g., a semantic feature), or a complicated feature (e.g., a deep hierarchical feature) of the specific sample image data. Based on the extracted image features, the preliminary model may determine a predicted output (i.e., a predicted body region) of the specific group of the training samples. The predicted output (i.e., the predicted body region) of the specific group of training samples may then be compared with the sample body region of the specific group of training samples based on a cost function. As used herein, a cost function of a machine learning model may be configured to assess a difference between a predicted output (e.g., a predicted body region) of the machine learning model and a desired output (e.g., a sample body region). If the value of the cost function exceeds a threshold in a current iteration, parameter values of the preliminary model may be adjusted and/or updated in order to decrease the value of the cost function (i.e., the difference between the predicted body region and the sample body region) to smaller than the threshold, and an intermediate model may be generated. Accordingly, in the next iteration, another group of training samples may be input into the intermediate model to train the intermediate model as described above.

The plurality of iterations may be performed to update the parameter values of the preliminary model (or the intermediate model) until a termination condition is satisfied. The termination condition may provide an indication of whether the preliminary model (or the intermediate model) is sufficiently trained. The termination condition may relate to the cost function or an iteration count of the iterative process or training process. For example, the termination condition may be satisfied if the value of the cost function associated with the preliminary model (or the intermediate model) is minimal or smaller than a threshold (e.g., a constant). As another example, the termination condition may be satisfied if the value of the cost function converges. The convergence may be deemed to have occurred if the variation of the values of the cost function in two or more consecutive iterations is smaller than a threshold (e.g., a constant). As still another example, the termination condition may be satisfied when a specified number (or count) of iterations are performed in the training process. The identification model may be determined based on the updated parameter values.

It should be noted that the above description is merely provided for the purposes of illustration, and not intended to limit the scope of the present disclosure. In some embodiments, a group of the plurality of groups of training samples may further include sample posture information of the sample subject, and the identification model may be obtained by training the preliminary model using the plurality of groups of training samples.

In some embodiments, the identification model may be updated from time to time, e.g., periodically or not, based on a sample set that is at least partially different from an original sample set from which an original identification model is determined. For instance, the identification model may be updated based on a sample set including new samples that are not in the original sample set, samples processed using an intermediate model of a prior version, or the like, or a combination thereof. In some embodiments, the determination and/or updating of the identification model may be performed on a processing device, while the application of the identification model may be performed on a different processing device. In some embodiments, the determination and/or updating of the identification mod& may be performed on a processing device of a system different than the medical system 100 or a server different than a server including the processing device 120 on which the application of the identification model is performed. For instance, the determination and/or updating of the identification model may be performed on a first system of a vendor who provides and/or maintains such an identification model and/or has access to training samples used to determine and/or update the identification model, while body region identification based on the provided identification model may be performed on a second system of a client of the vendor. In some embodiments, the determination and/or updating of the identification model may be performed online in response to a request for body region identification. In some embodiments, the determination and/or updating of the identification model may be performed offline.

Alternatively or additionally, the processing device 120 may identify the at least one scan area of the subject based on element information associated with at least one element of the image data of the subject. In some embodiments, the processing device 120 may obtain the element information associated with the at least one element of the image data. The processing device 120 may further identify the at least one scan area of the subject based on the element information. As used herein, an element of image data refers to a pixel or a voxel of the image data. The element information of the element may include a gray value of the element or a Hounsfield unit (HU) value corresponding to the element. As used herein, Hounsfield unit (HU) refers to a dimensionless unit used in computed tomography (CT) scanning to express CT numbers in a standardized and convenient form. Merely by way of example, the CT Hounsfield scale may be calibrated such that the HU value for water is 0 HU and that for air is −1000 HU. The HU value of an element may correspond to an X-ray beam absorption (or tissue density) of the element. The HU value of an element may indicate the type of tissue to which the element belongs. Elements with similar HU values may belong to similar tissue types. Merely by way of example, more dense tissue (e.g., a skeleton), with greater X-ray beam absorption, may have positive values and appears bright in a CT image; while less dense tissue (e.g., a lung filled with gas), with less X-ray beam absorption, may have negative values and appears dark in a CT image. In some embodiments, the HU value of an element may be represented as a gray value of the element on a visual interface (e.g., the screen of the user terminal). A higher HU value of an element may correspond to a higher gray value and a brighter element in a CT image.

After the at least one scan area of the subject is identified, the processing device 120 may further determine the scan range of the subject based on the at least one scan area of the subject. For example, the processing device 120 may determine a range that encloses the at least one scan area as the scan range of the subject. For illustration purposes, if the scan areas of the subject include the head, the chest, and the abdomen of the subject, a range from the head to the abdomen of the subject may be determined as the scan range of the subject.

In 530, the processing device 120 (e.g., the determination module 420) may determine at least one parameter value of at least one scan parameter based on the at least one scan area of the subject.

The scan parameter(s) may include, for example, a voltage of a radiation source, a current of the radiation source, a distance between the radiation source and a detector (also referred to as a source image distance, or a SID), a radiation dose, a scan time, a field of view (FOV) or the like, or any combination thereof.

In some embodiments, the processing device 120 may obtain a scan protocol of the subject based on the scan area of the subject. The scan protocol may include, for example, value(s) or value range(s) of scan parameter(s), a portion of the subject to be scanned, feature information of the subject (e.g., the gender, the body shape), or the like, or any combination thereof. For example, if the scan area of the subject is the chest, a scan protocol corresponding to a chest examination may be obtained. Further, the processing device 120 may determine the at least one parameter value of at least one scan parameter based on the scan protocol of the subject. The scan protocol may be previously generated (e.g., manually input by a user or determined by the processing device 120) and stored in a storage device. The processing device 120 may retrieve the scan protocol from the storage device, and determine the at least one parameter value of at least one scan parameter based on the scan protocol.

In some embodiments, the processing device 120 may determine the at least one parameter value of the at least one scan parameter based on the at least one scan area of the subject and a relationship between a scan area and at least one scan parameter. For example, the relationship may be represented in the form of a table recording different scan areas and their corresponding value(s) of the scan parameter(s). The relationship between the scan area and the scan parameter(s) may be stored in a storage device, and the processing device 120 may retrieve the relationship from the storage device. In some embodiments, the relationship between the scan area and the scan parameter(s) may be determined by the processing device 120 based on experimental data. For example, a relationship between the chest and the scan parameter(s) may be obtained or determined by performing a plurality of simulation scans on the chest of the subject.

In some embodiments, after the at least one parameter value of the at least one scan parameter is determined based on the at least one scan area of the subject, the processing device 120 may further adjust the at least one parameter value of the at least one scan parameter based on feature information of the subject. The feature information of the subject may include a width, a height, a thickness, posture information, or the like, of the subject or a portion of the subject. In some embodiments, the feature information of the subject may be previously determined and stored in a storage device (e.g., the storage device 130, the storage 220, the storage 390, or an external source). The processing device 120 may retrieve the feature information of the subject from the storage device. Additionally or alternatively, the feature information (e.g., the posture information) of the subject may be determined based on image data of the subject according to an image analysis algorithm (e.g., an image segmentation algorithm, a feature point extraction algorithm).

For illustration purposes, the processing device 120 may determine initial parameter value(s) of the scan parameter(s) based on the scan area of the subject. The processing device 120 may determine whether the height (or the width, the thickness) of the subject is within a preset range. In response to determining that the height (or the width, the thickness) of the subject is not within the preset range, the processing device 120 may adjust (e.g., increase, decrease) the initial parameter value(s) of the initial scan parameter(s) to determine the parameter value(s) of the scan parameter(s). As another example, the processing device 120 may determine whether the hands of the subject are placed on two sides of the subject's body. In response to determining that the hands of the subject are not located on the two sides of the subject's body, the processing device 120 may designate the initial parameter value(s) of the scan parameter(s) as the parameter value(s) of the scan parameter(s). In response to determining that the hands of the subject are located on the two sides of the subject's body, the processing device 120 may adjust (e.g., increase) the initial parameter value(s) of the initial scan parameter(s) to determine the parameter value(s) of the scan parameter(s).

In some embodiments, the processing device 120 may obtain a plurality of historical scan protocols of a plurality of historical scans performed on the same subject or one or more other subjects (each referred to as a sample subject). Each of the plurality of historical scan protocols may include at least one historical parameter value of the at least one scan parameter relating to a historical scan performed on a sample subject, wherein the historical scan is of a same type of scan as the scan to be performed on the subject. Optionally, each historical scan protocol may further include feature information relating to the corresponding sample subject (e.g., the gender of the sample subject, the body shape, size, etc., of the sample subject).

In some embodiments, the processing device 120 may select one or more historical scan protocols from the plurality of historical scan protocols based on the scan area of the subject, the feature information of the subject, and the information relating to the sample subject of each historical scan protocol. Merely by way of example, the processing device 120 may select one historical scan protocol, the sample subject of which has the highest degree of similarity as the subject, among the plurality of historical scan protocols. The degree of similarity between a sample subject and the subject may be determined based on the feature information of the sample subject and the feature information of the subject. For a certain scan parameter, the processing device 120 may further designate the historical parameter value of the certain scan parameter in the selected historical scan protocol as the parameter value of the scan parameter. As another example, the processing device 120 may modify the historical parameter value of the certain scan parameter in the selected historical scan protocol based on the feature information of the subject and the sample subject, for example, a thickness difference between the subject and the sample subject. The processing device 120 may further designate the modified historical parameter value of the certain scan parameter as the parameter value of the certain scan parameter.

In 540, the processing device 120 (e.g., the control module 430) may cause the medical device to scan the subject based on the scan range and the at least one parameter value of the at least one scan parameter.

For example, the processing device 120 may cause the medica device to scan the subject from the scan start position to the scan end position using the at least one parameter value of the at least one scan parameter. As another example, the processing device 120 may cause the medical device to scan the subject with the scan center position as the center.

In some embodiments, the scan range may correspond to a plurality of scan areas. Different scan areas may correspond to different parameter values of scan parameters. During the scan of the plurality of scan areas of the subject, the parameter value(s) of the scan parameter(s) may be adjusted based on the scan area. For illustration purposes, if the scan range of the subject corresponds to a first scan area (e.g., the head) and a second scan area (e.g., the abdomen), the first scan area corresponds to a first set of parameter values of the scan parameters, and the second scan area corresponds to a second set of parameter values of the scan parameters, the processing device 120 may cause the medical device to scan the first scan area according to the first set of parameter values of the scan parameters, and scan the second scan area according to the second set of parameter values of the scan parameters.

According to some embodiments of the present disclosure, one or more scan areas of a subject may be determined based on image data of the subject. In addition, parameter value(s) of scan parameter(s) corresponding to each scan area of the one or more scan areas may further be determined. The systems and methods disclosed herein for scan parameter determination for different scan areas may be implemented with reduced or minimal or without user intervention. A plurality of scan areas of the subject may be imaged in one scan using different sets of parameter value(s) of scan parameter(s). Compared with conventional ways, the systems and methods disclosed herein are more efficient and accurate by, e.g., reducing the workload of a user, cross-user variations, and the time needed for the scan.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

In some embodiments, before the scan is performed on the subject, the processing device 120 may perform one or more additional operations. In some embodiments, the processing device 120 may determine posture information of the subject. The processing device 120 may then determine the scan range of the subject based on the image data and the posture information as described in connection with operation 520. More descriptions for determining the posture information may be found elsewhere in the present disclosure (e.g., FIG. 6, and the descriptions thereof).

In some embodiments, a subject positioning process may be added before operation 540. For example, the processing device 120 may identify at least one feature point in the image data. The feature point may correspond to a point of interest (POI) of the subject, such as an anatomical joint (e.g., a shoulder joint, a knee joint, an elbow joint, an ankle joint, a wrist joint) or another specific physical point in a body region (e.g., the head, the neck, a hand, a leg, a foot, a spine, a pelvis, a hip) of the subject. In some embodiments, the feature point may correspond to the scan start position, the scan center position, the scan end position, or the like, of the scan to be performed on the subject. In some embodiments, the at least one feature point may be identified manually by a user (e.g., a doctor, an operator, a technician). For instance, the user may specify the at least one feature point on an interface (e.g., implemented on a terminal device 140) that displays the image data. Alternatively, the at least one feature point may be generated by a computing device (e.g., the processing device 120) automatically according to an image analysis algorithm (e.g., an image segmentation algorithm, a feature point extraction algorithm).

The processing device 120 may then determine a target position of the subject based on the at least one feature point. As used herein, a target position of a subject refers to an estimated position where the subject needs to be located during the scan of the subject according to, for example, posture information of the subject and/or a scan area of the subject. In some embodiments, if the feature point corresponds to the scan start position, the scan center position, or the scan end position, the processing device 120 may determine, based on the feature point, the target position of the subject at which the POI of the subject is located within a detection region (e.g., the detection region 113) of the medical device. For example, if the feature point corresponds to the scan start position or the scan center position, the processing device 120 may determine, based on the feature point, the target position of the subject at which the POI of the subject is coincident with a center point of the detection region (e.g., the detection region 113) of the medical device.

The processing device 120 may further cause the medical device to move the subject to the target position. For example, the processing device 120 may cause a scanning table (e.g., the scanning table 114) to move the subject to the target position of the subject. When the subject is located at its target position, the processing device 120 may cause the medical device to scan the subject based on the scan range and the at least one parameter value of the at least one scan parameter as described in connection with operation 540. For example, if a first feature point corresponding to the scan start position and a second feature point corresponding to the scan end position are identified, the processing device 120 may cause the medical device to scan the subject from the scan start position to the scan end position. As another example, if only one feature point corresponding to the scan start position is identified, the processing device 120 may cause the medical device to scan the subject from the scan start position, and determine whether the scan ends based on real-time image data of the subject generated based on the scan of the subject. Specifically, the processing device 120 may determine whether the real-time image data of the subject includes a representation of a scan area of the subject. In response to determining that the real-time image data of the subject does not include the representation of the scan area of the subject, the processing device 120 may determine that the scan ends.

In some embodiments, the processing device 120 may generate an image of the subject based on the scan of the subject by the medical device. The processing device 120 may adjust the at least one parameter value of the at least one scan parameter based on the image. For illustration purposes, a CT scan may be performed on the subject by a CT device, and a CT image providing accurate information of the internal structure of the subject may be generated based on the CT scan of the subject. The processing device 120 may adjust the scan range (e.g., the scan end position) of the subject based on the CT image. Specifically, the processing device 120 may identify the at least one scan area of the subject based on the CT image using the identification model as described elsewhere in the present disclosure, and adjust the scan range (e.g., the scan end position) of the subject based on the at least one identified scan area. Additionally or alternatively, the scan range (e.g., the scan end position) of the subject may be manually adjusted by a user of the medical system 100 based on the CT image. According to some embodiments of the present disclosure, the at least one parameter value of the at least one scan parameter may be dynamically adjusted based on the image generated based on the scan of the subject. Therefore, appropriate parameter value(s) of the scan parameter(s) may be determined, which may ensure the image quality of the subject, and improve the accuracy of clinical diagnosis performed on the basis of the image.

In some embodiments, the processing device 120 may determine at least one reconstruction parameter corresponding to the at least one scan area of the subject. The processing device 120 may generate an image of the subject based on the scan of the subject by the medical device and the at least one reconstruction parameter. In some embodiments, for images corresponding to different scan areas of the subject, different reconstruction parameters may be applied to achieve a good image quality. For example, a bone induced artifact correction algorithm may be applied in the reconstruction of an image of the head of the subject. As another example, a high-contrast algorithm may be applied in the reconstruction of an image of the abdomen of the subject. According to some embodiments of the present disclosure, the at least one reconstruction parameter corresponding to the at least one scan area of the subject may be automatically determined, and the image of the subject may further be reconstructed based on the at least one reconstruction parameter, which may achieve an automated reconstruction parameter determination. In addition, a plurality of scan areas of the subject may be imaged and reconstructed in one scan using different sets of parameter value(s) of scan parameter(s) and different reconstruction parameters.

In some embodiments, the scan of the subject may be a CT scan or an MRI scan, and the image of the subject may be a CT image or an MRI image. The anatomical image, such as the CT image or the MRI image, may provide anatomical data of the subject, and be applied in attenuation correction of a functional image of the subject (e.g., the PET image). The processing device 120 may then obtain PET scan data by performing, based on the scan range, a PET scan of the subject using a PET device. The processing device 120 may further perform an attenuation correction on the PET scan data based on the CT image or the MRI image. For example, the processing device 120 may determine tissue attenuation coefficients corresponding to different portions (e.g., different organs, different tissues) of the subject based on the CT image. The processing device 120 may generate an attenuation map corresponding to the 511 KeV photon rays (e.g., γ rays) based on the tissue attenuation coefficients. The processing device 120 may then correct the PET image based on the attenuation map. Specifically, the PET image may be expressed in the form of a first matrix including a plurality of first elements. The attenuation map associated with the PET image may be expressed in the form of a second matrix including a plurality of second elements. One of the plurality of second elements may correspond to one or more of the plurality of first elements. A corrected PET image may be generated by multiplying each of the plurality of first elements with a corresponding second element.

Figure 6:
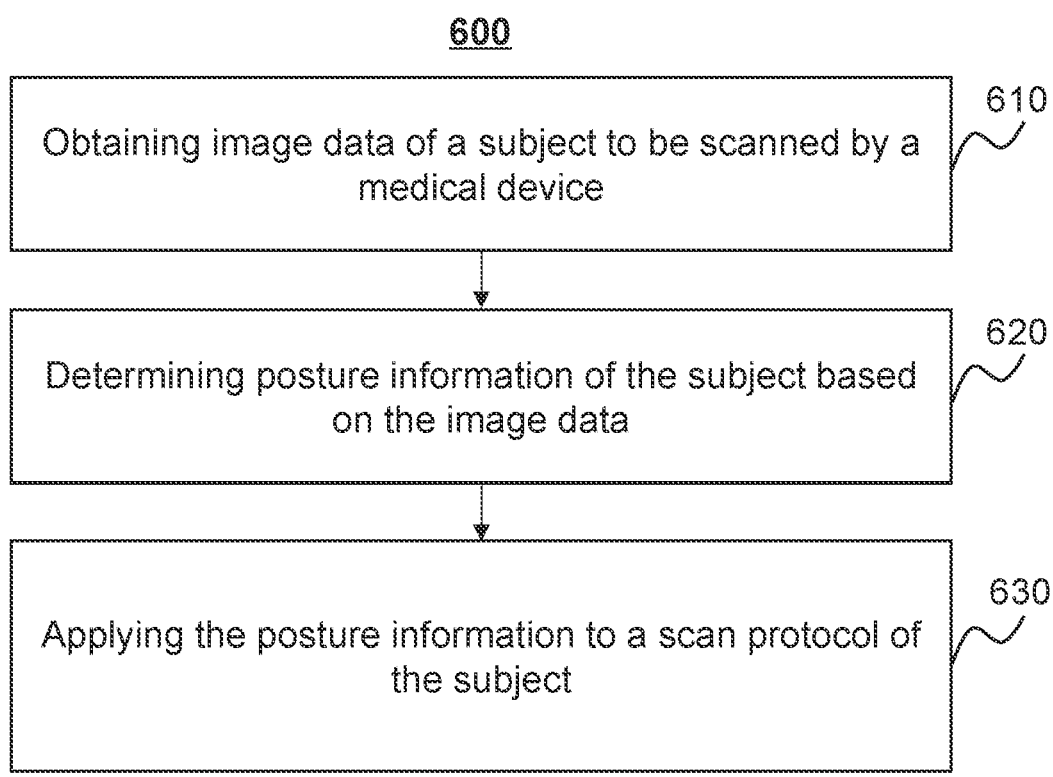
FIG. 6 is a flowchart illustrating an exemplary process for determining posture information of a subject according to some embodiments of the present disclosure.

FIG. 6 is a flowchart illustrating an exemplary process for determining posture information of a subject according to some embodiments of the present disclosure. In some embodiments, the process 600 may be implemented in the medical system 100 illustrated in FIG. 1. For example, the process 600 may be stored in the storage device 130 and/or the storage (e.g., the storage 220, the storage 390) as a form of instructions, and invoked and/or executed by the processing device 120 (e.g., the processor 210 of the computing device 200 as illustrated in FIG. 2, the CPU 340 of the mobile device 300 as illustrated in FIG. 3), The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In 610, the processing device 120 (e.g., the obtaining module 410) may obtain image data of a subject to be scanned by a medical device.

Operation 610 may be performed in a similar manner as operation 510 as described in connection with FIG. 5, and the descriptions thereof are not repeated here.

In 620, the processing device 120 (e.g., the determination module 420) may determine posture information of the subject based on the image data.

Exemplary posture information may include a head first-supine (HFS) posture, a head first-prone (HFP) posture, a head first-decubitus right (HFDR) posture, a head first-decubitus left (HFDL) posture, a feet first-decubitus right (FFDR) posture, a feet first-decubitus left (FFDL) posture, a feet first-prone (FFP) posture, a feet first-supine (FFS) posture, or the like.

In some embodiments, the processing device 120 may determine the posture information of the subject based on the image data according to an image analysis algorithm. For example, the processing device 120 may determine one or more parameter values of one or more posture parameters of the subject based on the image data according to an image segmentation algorithm and/or a feature point extraction algorithm. Exemplary posture parameter(s) may include a position (e.g., a coordinate in a coordinate system) of a portion (e.g., the head, the neck, a hand, a leg, and/or a foot) of the subject, a joint angle of a joint (e.g., a shoulder joint, a knee joint, an elbow joint, and/or an ankle joint) of the subject, a shape and/or a size of a portion of the subject, a height of the entire subject or a portion (e.g., the upper body, the lower body) of the subject, or the like, or any combination thereof. Exemplary image segmentation algorithms may include a region-based algorithm (e.g., a threshold segmentation, a region-growth segmentation), an edge detection segmentation algorithm, a compression-based algorithm, a histogram-based algorithm, a dual clustering algorithm, or the like. Exemplary feature extraction algorithms may include a principal component analysis (PCA), a linear discriminant analysis (LDA), an independent component analysis (ICA), a multi-dimensional scaling (MDS) algorithm, a discrete cosine transform (DCT) algorithm, or the like, or any combination thereof. Further, the processing device 120 may determine the posture information of the subject based on the one or more parameter values of the one or more posture parameters of the subject.

Additionally or alternatively, the processing device 120 may determine the posture information of the subject using a posture determination model. The posture determination model refers to a model (e.g., a machine learning model) or an algorithm for determining posture information of a subject based on image data of the subject. For example, the processing device 120 may input the image data of the subject into the posture determination model, and the posture determination model may output the posture information of the subject by processing the image data. The training of the posture determination model may be performed in a similar manner with that of the identification model as described in connection with operation 520, and the descriptions thereof are not repeated here.

In some embodiments, the processing device 120 may cause a voice processing device to transmit the posture information to a user (e.g., a doctor, an operator). For example, the processing device 120 may cause the voice processing device to broadcast the posture information to the user. More descriptions of the voice processing device may be found elsewhere in the present disclosure (e.g., FIG. 1, and the descriptions thereof). In some embodiments, the processing device 120 may cause a terminal device to display the posture information to the user. For example, the processing device 120 may cause a display screen of the terminal device to display the posture information to the user. According to some embodiments of the present disclosure, the posture information of the subject may be displayed to the user in real time, and the user may see the posture information of the subject via the terminal device clearly and intuitively, which may facilitate the user to perform other operations, and improve the scanning efficiency. In addition, the posture information of the subject may be transmitted to the user via a voice broadcasting. One or more users located at different positions may know the posture information of the subject without standing in front of the terminal device.

In some embodiments, the processing device 120 may obtain, via the terminal device or the voice processing device, an input relating to the posture information of the subject from the user. The input may be in any form. For example, the input may be a voice input. A voice collection mode may be activated on the terminal device or the voice processing device to obtain the voice input from the user. Further, the processing device 120 may receive the voice input from the terminal device or the voice processing device. Optionally, the processing device 120 may convert the voice input to a text input, and cause the terminal device to display the text input. As another example, a text input mode may be activated on the terminal device or the voice processing device, and a text input may be collected and transmitted to processing device 120.

In some embodiments, the input may be associated with the posture information of the subject determined by the user. For example, the terminal device may display the image data of the subject, and the user may select (e.g., by clicking an icon corresponding to) a specific posture from a plurality of postures for the subject via an input component of the terminal device (e.g., a mouse, a touch screen). As another example, the user may see the subject directly and determine posture information of the subject without displaying the image data of the subject by the terminal device.

Further, the processing device 120 may update the posture information of the subject based on the input. For example, the processing device 120 may compare the posture information of the subject and the input of the user to generate a comparison result. The processing device may update the posture information of the subject based on the comparison result. For illustration purposes, the processing device 120 may determine first posture information of the subject based on the image data of the subject. The processing device 120 may determine second posture information based on the input of the user. The processing device 120 may then determine whether the first posture information is the same as the second posture information. If the first posture information is the same as the second posture information, the processing device 120 may determine that the first posture information (or the second posture information) is final posture information. In such cases, the accuracy of the determination of the posture information may be improved. If the first posture information is different from the second posture information, the processing device 120 may re-identify the first and second posture information and/or generate a reminder regarding the comparison result. The reminder may be in the form of text, voice, an image, a video, a haptic alert, or the like, or any combination thereof. For example, the processing device 120 may transmit the reminder to a terminal device (e.g., the terminal device 140) of a user (e.g., a doctor) of the medical system 100. The terminal device may output the reminder to the user. Optionally, the user may input an instruction or information in response to the reminder. Merely by way of example, the user may manually select the final posture information from the first posture information and the second posture information. For example, the processing device 120 may cause the terminal device to display information (e.g., the image data, the comparison result) of the first posture information and the second posture information. The user may select the final posture information from the first posture information and the second posture information based on the information of the first posture information and the second posture information.

In 630, the processing device 120 (e.g., the determination module 420) may apply the posture information to a scan protocol of the subject.

In some embodiments, the scan protocol may include a digital imaging and communications in medicine (DICOM). The DICOM refers to a standard for image data storage and transfer. The DICOM may use a specific file format and a communication protocol to define a medical image format that can be used for data exchange with a quality that meets clinical needs.

In some embodiments, the processing device 120 may obtain the scan protocol of the subject. The scan protocol may be previously generated (e.g., manually input by a user or determined by the processing device 120) and stored in a storage device. The processing device 120 may retrieve the scan protocol from the storage device. The processing device 120 may determine whether the scan protocol includes preset posture information. In response to determining that the scan protocol does not include the preset posture information, the processing device 120 may apply the posture information to the scan protocol. In response to determining that the scan protocol includes the preset posture information, the processing device 120 may update the preset posture information based on the posture information. For example, the processing device 120 may delete the preset posture information from the scan protocol, and store the posture information in the scan protocol.

In some embodiments, the processing device 120 may store the posture information of the subject in one or more storage device (e.g., the storage device 130) of the medical system 100 or an external storage device. After a scan is performed on the subject, the processing device 120 may access the storage device and retrieve the posture information for further processing. For example, the processing device 120 may add at least one annotation indicating the posture information of the subject on an image generated based on the scan of the subject, and transmit the image with the at least one annotation to the terminal device for display. For example, an annotation "HFS" representing that the posture of the subject is the head first-supine posture may be added to the image.

According to some embodiments of the present disclosure, the posture information of the subject may be determined based on the image data, and the posture information may be stored in the scan protocol of the subject. Compared to a conventional way that a user needs to manually determine the posture information of the subject, the automated posture information determination systems and methods disclosed herein may be more accurate and efficient by, e.g., reducing the workload of a user, cross-user variations, and the time needed for the selection of the posture information of the subject. In addition, the annotation indicating the posture information of the subject may be added on the image generated based on the scan of the subject, and accordingly, the user may process the image more accurately and efficiently. Furthermore, a disease diagnosis operation may be performed on the subject based on the image accurately, and the probability of misdiagnosis may be reduced.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 120 may perform one or more image processing operations on the image generated based on the scan of the subject according to an image display convention or a reading habit of a user (e.g., a doctor). Exemplary image processing operations may include an image segmentation operation, an image classification operation, an image recognition operation, an image registration operation, an image fusion operation, an image binarization operation, an image scaling operation, an image rotation operation, an image cropping operation, a window width and/or window level adjustment operation, a brightness adjustment operation, a grayscale adjustment operation, a histogram operation, or the like. Further, a disease diagnosis operation may be performed on the subject based on the processed image by the user or the one or more components (e.g., the processing device 120) of the medical system 100.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A method implemented on a computing device having at least one processor and at least one storage device, the method comprising:
   obtaining image data of a subject to be scanned by a medical device;
   determining a scan range of the subject based on the image data, wherein the scan range includes a plurality of scan areas of the subject;
   setting scan parameters of the plurality of scan areas of the subject with different sets of parameter values; and
   performing, by the medical device, an imaging on the plurality of scan areas based on the different sets of parameter values of scan parameters in one scan.

2. The method of claim 1, wherein the image data of the subject is obtained by an image capturing device or the medical device.

3. The method of claim 1, wherein the determining a scan range of the subject based on the image data comprises:
   identifying the plurality of scan areas of the subject based on the image data of the subject using an identification model; and
   determining the scan range of the subject based on the plurality of scan areas of the subject.

4. The method of claim 1, wherein the determining a scan range of the subject based on the image data comprises:
   obtaining element information associated with at least one element of the image data;
   identifying the plurality of scan areas of the subject based on the element information; and
   determining the scan range of the subject based on the plurality of scan areas of the subject.

5. The method of claim 1, wherein the setting scan parameters of the plurality of scan areas of the subject with different sets of parameter values comprises:
   for each scan area of the plurality of scan areas,
      obtaining a relationship between the scan area and at least one scan parameter of the scan area; and
      determining at least one parameter value of the at least one scan parameter based on the scan area and the relationship.

6. The method of claim 1, further comprising:
   identifying at least one feature point in the image data;
   determining a target position of the subject based on the at least one feature point; and
   causing the medical device to move the subject to the target position.

7. The method of claim 1, further comprising:
   generating an image of the subject based on the scan of the subject by the medical device; and
   adjusting the parameter values of the scan parameters based on the image.

8. The method of claim 1, further comprising:
   determining a plurality of reconstruction parameters corresponding to the plurality of scan areas of the subject; and
   generating an image of the subject based on the scan of the subject by the medical device and the plurality of reconstruction parameters.

9. The method of claim 8, wherein
   the scan of the subject is a computed tomography (CT) scan or a magnetic resonance imaging (MRI) scan,
   the image of the subject is a CT image or an MRI image, and
   the method further comprises:
      obtaining PET scan data by performing, based on the scan range, a PET scan of the subject using a PET device; and
      performing an attenuation correction on the PET scan data based on the CT image or the MRI image.

10. The method of claim 1, further comprising:
    determining posture information of the subject based on the image data;
    applying the posture information to a scan protocol of the subject.

11. The method of claim 10, wherein the applying the posture information to a scan protocol of the subject comprises:
    obtaining the scan protocol of the subject; and
    determining whether the scan protocol includes preset posture information.

12. The method of claim 11, further comprising:
    in response to determining that the scan protocol does not include the preset posture information, storing the posture information in the scan protocol.

13. The method of claim 11, further comprising:
    in response to determining that the scan protocol includes the preset posture information, updating the preset posture information based on the posture information.

14. The method of claim 10, further comprising:
    causing a voice processing device to transmit the posture information to a user; or
    causing a terminal device to display the posture information to the user.

15. The method of claim 14, wherein the determining posture information of the subject based on the image data comprises:
    obtaining, via the terminal device or the voice processing device, an input relating to the posture information of the subject from the user; and
    updating the posture information of the subject based on the input.

16. The method of claim 15, wherein the updating the posture information of the subject based on the input comprises:
    comparing the posture information of the subject and the input of the user to generate a comparison result; and
    updating the posture information of the subject based on the comparison result.

17. A method implemented on a computing device having at least one processor and at least one storage device, the method comprising:
    obtaining image data of a subject to be scanned by a medical device;
    determining posture information of the subject based on the image data; and
    applying the posture information to a scan protocol of the subject by:
       obtaining the scan protocol of the subject;
       determining whether the scan protocol includes preset posture information; and
       in response to determining that the scan protocol does not include the preset posture information, storing the posture information in the scan protocol, or in response to determining that the scan protocol includes the preset posture information, updating the preset posture information based on the posture information.

18. The method of claim 17, further comprising:
causing a voice processing device to transmit the posture information to a user; or
causing a terminal device to display the posture information to the user.

19. The method of claim 18, wherein the determining posture information of the subject based on the image data comprises:
obtaining, via the terminal device or the voice processing device, an input relating to the posture information of the subject from the user; and
updating the posture information of the subject based on the input.

20. A system, comprising:
at least one storage device storing a set of instructions; and
at least one processor in communication with the at least one storage device, when executing the stored set of instructions, the at least one processor causes the system to perform operations including:
 obtaining image data of a subject to be scanned by a medical device;
 determining a scan range of the subject based on the image data, wherein the scan range includes a plurality of scan areas of the subject;
 setting scan parameters of the plurality of scan areas of the subject with different sets of parameter values; and
 performing, by the medical device, an imaging on the plurality of scan areas based on the different sets of parameter values of scan parameters in one scan.

* * * * *